US009462988B2

(12) United States Patent
Hansis (10) Patent No.: US 9,462,988 B2
(45) Date of Patent: Oct. 11, 2016

(54) TRUNCATION COMPENSATION FOR ITERATIVE CONE-BEAM CT RECONSTRUCTION FOR SPECT/CT SYSTEMS

(75) Inventor: Eberhard Sebastian Hansis, Menlo Park, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 263 days.

(21) Appl. No.: 13/979,142

(22) PCT Filed: Jan. 18, 2012

(86) PCT No.: PCT/IB2012/050239
§ 371 (c)(1),
(2), (4) Date: Jul. 11, 2013

(87) PCT Pub. No.: WO2012/101548
PCT Pub. Date: Aug. 2, 2012

(65) Prior Publication Data
US 2013/0294570 A1  Nov. 7, 2013

Related U.S. Application Data

(60) Provisional application No. 61/436,714, filed on Jan. 27, 2011.

(51) Int. Cl.
*A61B 6/02* (2006.01)
*A61B 6/03* (2006.01)
(Continued)

(52) U.S. Cl.
CPC ............. *A61B 6/5294* (2013.01); *A61B 6/488* (2013.01); *A61B 6/5235* (2013.01);
(Continued)

(58) Field of Classification Search
CPC .......... A61B 6/02; A61B 6/025; A61B 6/03; A61B 6/032; A61B 6/037; A61B 6/04; A61B 6/488; A61B 6/52; A61B 6/5211; A61B 6/5229; A61B 6/5235; A61B 6/5258; A61B 6/5294; G06T 7/00; G06T 7/0012; G06T 7/0022; G06T 7/0024; G06T 7/0026; G06T 7/0028; G06T 7/003; G06T 7/0032; G06T 7/0034; G06T 7/004; G06T 7/0042; G06T 7/0044; G06T 7/0046; G06T 7/0048; G06T 7/0051; G06T 7/0065; G06T 7/0067; G06T 7/60; G06T 7/602; G06K 9/20; G06K 9/2054; G06K 9/32; G06K 9/3233; G06K 9/62; G06K 9/6201; G06K 9/6202; G06K 9/6203; G06K 9/6204; G06K 9/6215; G06K 9/78; G06K 9/80; G06K 2009/6213

See application file for complete search history.

(56) References Cited

U.S. PATENT DOCUMENTS 6,339,223 B1  1/2002  Motomura et al.
6,810,102 B2  10/2004  Hsieh et al.
(Continued)

FOREIGN PATENT DOCUMENTS

JP  2002209880  7/2002
JP  2004073432  3/2004
(Continued)

OTHER PUBLICATIONS

Hansis, E., et al.; High Quality 3-D Coronary Artery Imaging on an Interventional C-arm X-ray System; 2010; Med. Phys.; 37(4)1601-1609.
(Continued)

*Primary Examiner* — Anastasia Midkiff (57) ABSTRACT

A multiple modality imaging system includes a cone-beam computed tomography scanner which acquires CT projection data of a subject in an examination region and a nuclear imaging scanner which concurrently/subsequently acquires nuclear projection data of the subject in the examination region. A CT reconstruction processor is programmed to perform the steps of: in the CT projection data, defining a field-of-view (FoV) with a voxel grid in a trans-axial direction; determining the subject's maximum trans-axial extents; generating an extending FoV by extending the voxel grid of the FoV to at least one extended region outside the FoV that encompass at least the determined maximum trans-axial extents and all attenuation in the trans-axial direction; and iteratively reconstructing the CT projection data into an attenuation map of the extended FoV. At least one nuclear reconstruction processor is programmed to correct the acquired nuclear projection data based on the iteratively reconstructed attenuation map.

18 Claims, 6 Drawing Sheets

(51) Int. Cl.

| | | |
|---|---|---|
| *G06T 7/00* | (2006.01) | |
| *G06T 7/60* | (2006.01) | |
| *G06K 9/32* | (2006.01) | |
| *G06K 9/78* | (2006.01) | |
| *G06K 9/80* | (2006.01) | |
| *A61B 6/00* | (2006.01) | |
| *G06K 9/62* | (2006.01) | |
| *G06K 9/20* | (2006.01) | |
| *G06T 11/00* | (2006.01) | |

(52) U.S. Cl.
CPC ......... *G06K 9/3233* (2013.01); *G06K 9/6202* (2013.01); *G06T 7/0044* (2013.01); *G06T 7/0046* (2013.01); *G06T 7/0048* (2013.01); *G06T 7/602* (2013.01); *A61B 6/032* (2013.01); *A61B 6/037* (2013.01); *A61B 6/5211* (2013.01); *A61B 6/5229* (2013.01); *G06K 9/2054* (2013.01); *G06K 9/32* (2013.01); *G06K 9/78* (2013.01); *G06K 9/80* (2013.01); *G06K 2009/6213* (2013.01); *G06T 7/0012* (2013.01); *G06T 11/005* (2013.01); *G06T 2211/432* (2013.01)

(56) References Cited

U.S. PATENT DOCUMENTS

| | | | |
|---|---|---|---|
| 6,907,102 B1 * | 6/2005 | Sauer et al. | .................... 378/19 |
| 7,440,535 B2 | 10/2008 | Netsch et al. | |
| 7,502,440 B2 | 3/2009 | Motomura et al. | |
| 7,660,379 B2 | 2/2010 | Scholz | |
| 7,737,406 B2 | 6/2010 | Vija et al. | |
| 7,756,315 B2 | 7/2010 | Hsieh et al. | |
| 7,876,946 B2 | 1/2011 | Scholz et al. | |
| 2005/0267348 A1 | 12/2005 | Wollenweber et al. | |
| 2007/0116344 A1 * | 5/2007 | Hsieh et al. | .................. 382/131 |
| 2009/0087062 A1 * | 4/2009 | Chu et al. | .................... 382/131 |
| 2012/0070057 A1 * | 3/2012 | Zhang et al. | ................. 382/131 |

FOREIGN PATENT DOCUMENTS

| | | |
|---|---|---|
| JP | 2006312027 | 11/2006 |
| JP | 2008-524575 | 7/2008 |
| JP | 2010500902 | 1/2010 |

OTHER PUBLICATIONS

Hansis, E., et al.; Iterative Reconstruction for circular Cone-Beam CT with an Offset Flat-Panel Detector; 2010; Nuclear Science Symposium Conference Record; pp. 2228-2231.

Knaup, M., et al.; Simple ROI Cone-Beam Computed Tomography; Proc. of First Intl. Conf. on Image Formation in X-Ray Computed Tomography; 2010; pp. 194-199.

Wiegert, J., et al.; Projection Extension for Region of Interest Imaging in Cone-Beam CT; 2005; Academic Radiology; 12(8)1010-1023.

* cited by examiner

TRUNCATION COMPENSATION FOR ITERATIVE CONE-BEAM CT RECONSTRUCTION FOR SPECT/CT SYSTEMS

CROSS REFERENCE TO RELATED APPLICATIONS

This application is a national filing of PCT application Serial No. PCT/IB2012/050239, filed Jan. 18, 2012, published as WO 2012/101548 A2 on Aug. 2, 2012, which claims the benefit of U.S. provisional application Ser. No. 61/436,714 filed Jan. 27, 2011, which is incorporated herein by reference.

The present application relates to medical imaging arts. It finds particular application in reconstruction schemes for x-ray computed tomography (CT) imaging. However, it also finds general application with other imaging modalities such as, but not limited to, single photon emission computed tomography (SPECT) and positron emission tomography (PET).

In diagnostic nuclear imaging, a radionuclide distribution is studied as it passes through a patient's bloodstream for imaging the circulatory system or for imaging specific organs that accumulate the injected radiopharmaceutical. Advantageously, the radiopharmaceutical can be designed to concentrate in selected tissues to provide preferential imaging of those selected tissues.

In single-photon emission computed tomography (SPECT), one or more radiation detectors, commonly called gamma cameras, are used to detect the radiopharmaceutical via radiation emission caused by radioactive decay events. Typically, each gamma camera includes a radiation detector array and a collimator disposed in front of the radiation detector array. The collimator defines a linear or small-angle conical line of sight so that the detected radiation comprises projection data. If the gamma cameras are moved over a range of angular views, for example over a 180° or 360° angular range, then the resulting projection data can be reconstructed into an image of the radiopharmaceutical distribution in the patient.

In positron emission tomography (PET), the radioactive decay events of the radiopharmaceutical produce positrons. Each positron interacts with an electron to produce a positron-electron annihilation event that emits two oppositely directed gamma rays. Using coincidence detection circuitry, a ring array of radiation detectors surrounding the imaging patient detect the coincident oppositely directed gamma ray events corresponding to the positron-electron annihilation. A line of response (LOR) connecting the two coincident detections contains the position of the positron-electron annihilation event. Such lines of response can be reconstructed to produce an image of the radiopharmaceutical distribution.

In time-of-flight PET (TOF-PET), the small time difference between the detection times of the two coincident γ ray events is used to localize the annihilation event along the LOR (line of response).

In computed tomography (CT) imaging, a radiation source irradiates an imaging subject; and a radiation detector array disposed on the opposite side of the imaging subject detects the transmitted radiation. Due to varying attenuations of radiation by tissues in the imaging subject, the detected radiation can be reconstructed into an image depicting radiation-absorbing structures in the imaging subject.

Reconstruction algorithms for nuclear emission tomography and x-ray transmission tomography include filtered back projection (FBP) or convolution backprojection methods and the associated filtering necessary to reconstruct emission and transmission projection data. FBP is an analytical method which takes a signal-to-detector approach. FBP is easily implemented, computationally fast, and generally linear. However, FBP has some limitations, more notably there are no provisions for modeling noise resulting from low photon counts at the detector, which hinders signal-to-noise ratio (SNR). One way to reduce image noise using FBP reconstruction is to use a higher radiation dose, which is a concern regarding patient safety.

Another class of reconstruction techniques are the iterative reconstruction methods, which uses a complex iterative algorithm that refines and builds the image representation and can accommodate corrections for attenuation, noise, scatter, detector efficiency, dead-time, anatomical models, patient motion, and radiotracer kinetics, and the like.

However, iterative reconstruction methods are prone to truncation errors. In principle, iterative reconstruction methods work by comparing simulated acquisitions of the reconstructed image with the measured data. For example, in the case of CT the method calculates line integrals of the reconstructed attenuation image and compares these to the measured attenuation. According to the difference between simulated data and measured data, the reconstructed image is refined in an iterative fashion, until the simulated data matches the measured data. In the case of a truncated reconstruction FoV (reconstruction volume) which does not encompass the whole imaged object, the measured data may contain attenuation that was originally located outside the reconstructed FoV. However, the iterative method, in matching simulated and measured attenuation given the fixed FoV, places this attenuation inside the FoV. This may lead to strong artifacts, such as streaking and shading. Truncation problems are especially severe for trans-axial truncation of the imaged object. Increasing the reconstruction FoV, to encompass the whole imaged object, removes truncation artifacts. Similar arguments apply for the case of emission tomography, where tracer activity is reconstructed instead of attenuation.

One problem with both SPECT and PET imaging techniques is that the photon absorption and scatter by the anatomy of the patient between the radionuclide and the detector distorts the resultant image. One technique uses x-ray CT scan data to generate an attenuation map. Since both x-rays and gamma rays are more strongly attenuated by hard tissue, such as bone or even synthetic implants, as compared to softer tissue, the CT data can be used to estimate an attenuation map for gamma rays emitted by the radiopharmaceutical. If the reconstructed attenuation map suffers from truncation errors, the errors will be carried into the corrected SPECT/PET projection data resulting in inaccurate reconstructed activity values.

The present application provides a new and improved system and method which overcomes the above-referenced problems and others.

In accordance with one aspect, a method for diagnostic imaging is presented. The method includes acquiring projection data of a subject situated in an examination region with a first imaging modality; defining a field-of-view (FoV) with a voxel grid in a trans-axial direction; determining the subject's maximum trans-axial extents; generating an extended FoV by extending the voxel grid of the FoV to at least one extended region outside the FoV that encompass at least the determined maximum trans-axial extents and attenuation in the trans-axial direction; and iteratively reconstructing the acquired projection data into an image representation of the extended FoV.

In accordance to another aspect, an imaging scanner is presented. The imaging scanner includes a first imaging scanner which acquires projection data of a subject situated in an examination region using a first imaging modality. At least one processor is programmed to perform the steps of: defining a field-of-view (FoV) with a voxel grid in a trans-axial direction; determining the subject's maximum trans-axial extents; generating an extending FoV by extending the voxel grid of the FoV to at least one extended region outside the FoV that encompass at least the determined maximum trans-axial extents and attenuation in the trans-axial direction; and iteratively reconstructing the acquired projection data into an image representation of the extended FoV.

In accordance with another aspect, a multiple modality imaging system is presented. The system includes a computed tomography scanner which acquires CT projection data of a subject in an examination region and a nuclear imaging scanner which acquires nuclear projection data of the subject in the examination region. At least one CT reconstruction processor is programmed to perform the steps of: in the CT projection data, defining a field-of-view (FoV) with a voxel grid in a trans-axial direction; determining the subject's maximum trans-axial extents; generating an extending FoV by extending the voxel grid of the FoV to at least one extended region outside the FoV that encompass at least the determined maximum trans-axial extents and all attenuation in the trans-axial direction; iteratively reconstructing the CT projection data into an attenuation map of the extended FoV; and correcting the nuclear projection data based on the iteratively reconstructed attenuation map.

One advantage is that field-of-view truncation errors are reduced.

Another advantage is that emission tomography data can be corrected more accurately for attenuation and scatter effects.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
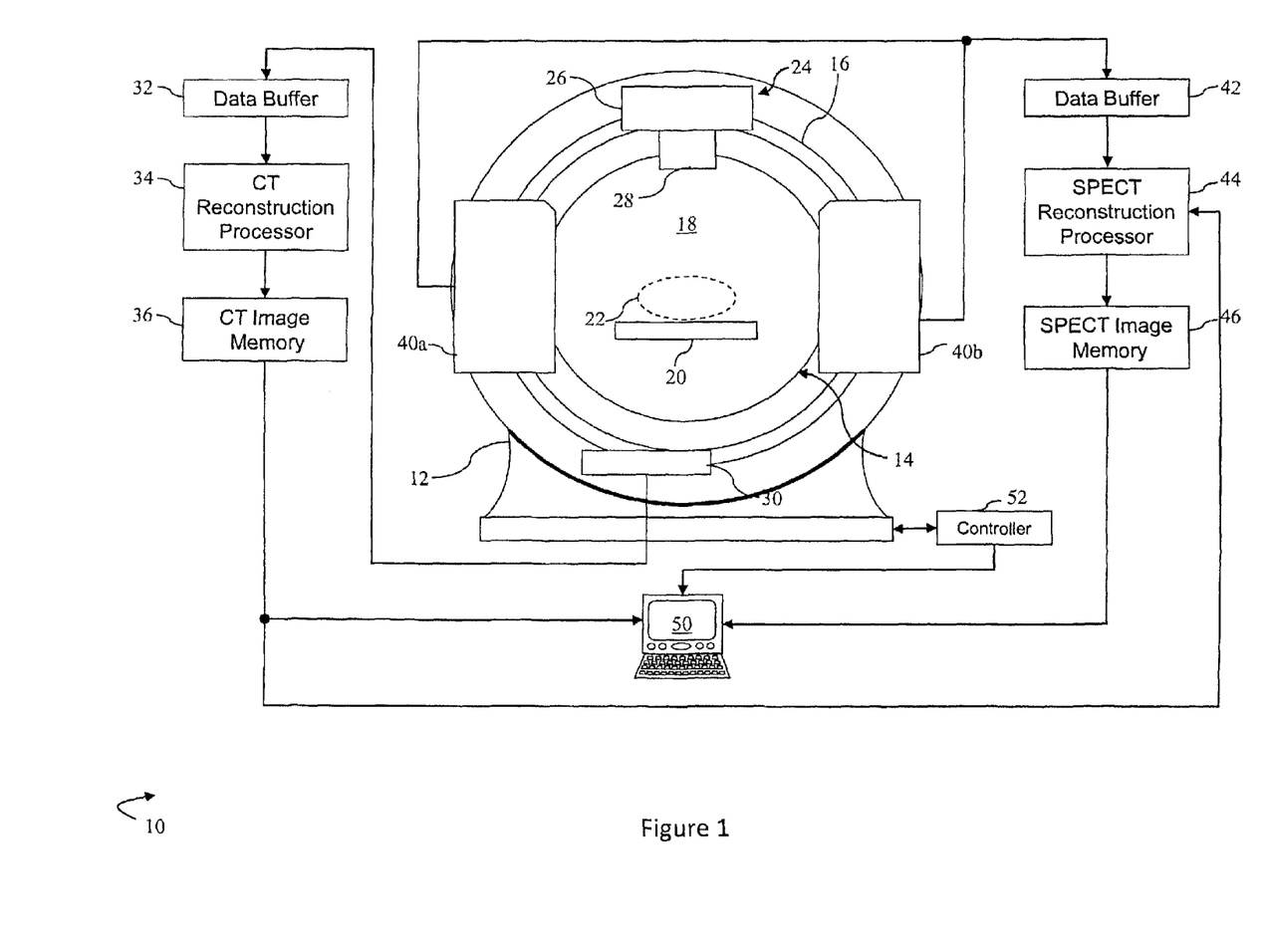
FIG. 1 is diagrammatic view of a combined SPECT/CT single gantry system.

With reference to FIG. 1, a diagnostic imaging system 10 performs concurrently and/or independently x-ray computed tomography (CT) and nuclear imaging, such as PET or SPECT. The imaging system 10 includes a stationary housing 12 which defines a patient receiving bore 14. A rotatable gantry 16, supported by the housing 12, is arranged for rotation around the bore to define a common examination region 18. A patient support 20, which supports a patient or subject 22 to be imaged and/or examined, is longitudinally and/or vertically adjusted to achieve the desired positioning of the patient in the examination region.

To provide CT imaging capabilities, an x-ray assembly 24 which is mounted on the rotatable gantry 16 includes an x-ray source 26, such as an x-ray tube, and a filter, collimator, and/or shutter assembly 28. The collimator collimates the radiation from the x-ray source 26 into a cone or wedge beam, one or more substantially parallel fan beams, or the like. The shutter gates the beam on and off. An x-ray detector 30, such as a solid state, flat panel detector, is mounted on the rotatable gantry 16 opposite the x-ray assembly 24. In the illustrated embodiment, the detector panel is offset relative to the projected center of radiation or transversely displaced from the center of rotation in the trans-axial plane. Offset detector geometries are desirable because they allow for an increased FoV or allow for smaller detectors sizes. Larger detectors tend to be more complex, expensive to manufacture, can limit the overall system design, and can limit detector positioning or patient access or the like. X-ray systems with a wide, non-offset detector that spans the full field-of-view are also contemplated.

As the gantry rotates, the x-ray assembly 24 and the x-ray detector 30 revolve in concert around the examination region 18 to acquire CT projection data spanning a full 360° revolution, multiple revolutions, or a smaller arc. Each CT projection indicates x-ray attenuation along a linear path between the x-ray assembly 24 and a detecting element of the x-ray detector 30. The acquired CT projection data is stored in a CT data buffer 32 and processed by a CT reconstruction processor 34 into a CT image representation and then stored in a CT image memory unit 36. Taken together, the x-ray source, the collimator/shutter assembly, the detector, and the reconstruction processor define a system or means for generating an anatomical, CT, x-ray, or first image.

To provide functional nuclear imaging capabilities, one or more nuclear detector heads 40a, 40b, such as single photon emission tomography (SPECT) detectors, are moveably mounted to the rotating gantry 16. Mounting the x-ray assembly 24 and the nuclear detector heads 40a, 40b on the same gantry permits the examination region 18 to be imaged by both modalities without moving the patient 22. In one embodiment, the detector heads are moveably supported by a robotic assembly (not shown) which is mounted to the rotating gantry 16. The robotic assembly enables the detector heads to be positioned at a selectable offset about the patient 22, e.g. 90° offset, 180° opposite each other, etc. Each SPECT detector head includes a collimator such that each detected radiation event is known to have originated along an identifiable linear or small-angle conical line of sight so that the acquired radiation comprises projection data. The acquired SPECT projection data is stored in a data buffer 42 and processed by a SPECT reconstruction processor 44 into a SPECT image representation and stored in a SPECT image memory unit 46. Taken together, the SPECT detector heads and the SPECT reconstruction processor define a system means for generating a nuclear, functional, or second image.

In another embodiment, the functional imaging system or means includes positron emission tomography (PET) detectors. One or more rings of PET detectors are arranged about the patient receiving bore 14 to receive gamma radiation therefrom. Detected pairs of coincident radiation events define LORs which are stored in list mode in a data buffer and processed by a PET reconstruction processor into a PET image representation and stored in a PET image memory unit. Taken together, the PET detector ring(s) and the PET reconstruction processor define the system or means for generating the functional image.

Filtered convolution backprojection (FBP) is commonly employed to reconstruct emission and transmission projection data. FBP is an analytical method which takes a signal-to-detector approach, i.e. it assumes that point-source radiation from a focal spot on the x-ray tube passing through as a single, thin line through the center of a voxel that goes to the center of each detector cell. FBP is easy to implement and computationally fast. However, FBP has some limitations, more notably there are no provisions for modeling noise resulting from low photon counts which hinders signal-to-noise ratio (SNR). To overcome image noise using FBP reconstruction, a higher radiation dose can be used which is a concern regarding patient safety.

An alternative technique is the iterative reconstruction method which uses a complex iterative algorithm, such as maximum likelihood expectation maximization (MLEM) or ordered subset expectation maximization (OSEM), which refines and builds the image representation and can accommodate processing steps to account for attenuation, scatter, noise, detector efficiency, dead-time, anatomical models, patient motion, and radiotracer kinetics, and the like. In an iterative algorithm, an initial estimate of the activity or attenuation in a FoV is made. In other words, an initial image representation is generated, e.g., from an FBP or assuming a homogeneous signal distribution. Projection data is calculated or forward projected from the initial image and compared to the corresponding acquired projection data. A difference between the calculated projection data and the actual projection data is back projected on to the initial image representation to update the image representation. The algorithm is iterated until the difference is minimized or an optimal solution is available.

Though iterative reconstruction methods have attractive properties, e.g., when dealing with noisy data they can generate reconstructions with lower noise than FBP, but they are prone to truncation errors.

Figure 2A:
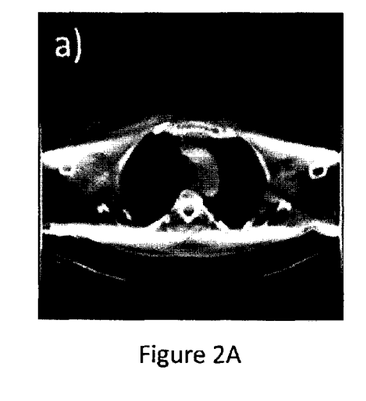
FIG. 2A is an image representation of an iterative reconstruction in a field of view that does not encompass the subject in the trans-axial direction causing strong artifacts.
Figure 2B:
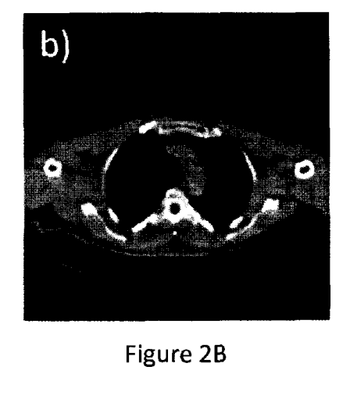
FIG. 2B is an image representation of an iterative reconstruction for which the reconstruction was carried out with an extended field of view to reduce truncation errors.
Figure 2C:
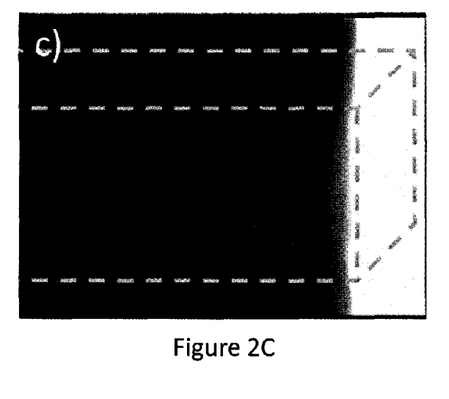
FIG. 2C is an image representation of a user selected field of view and an extend field of view.

The FoV with a selected voxel grid is selected by a user or a clinician and the extended FoV (ex-FoV) which includes extended regions outside of the FoV is determined. To compensate for truncation errors, the CT reconstruction processor 34 automatically extends the field-of-view (FoV) during reconstruction such that it includes the entire subject in the trans-axial direction to account for all attenuation that is present in the CT projection data or all activity that is present in the PET/SPECT projection data.

In one embodiment for determining the ex-FoV, the FoV is forward-projected on the acquired X-ray projection data to define the FoV 'footprint'. The presence of a substantial amount of attenuation or activity outside the FoV footprint in the trans-axial direction indicates truncation. The ex-FoV is then selected large enough such that it encompasses all attenuation or activity present in all projections in the trans-axial direction. This method may not be applicable if the subject extends beyond the detector in the trans-axial direction, i.e. the subject extends beyond the scanner FoV in which case one of the following methods for determining the ex-FoV can be used.

In another embodiment, the subject's trans-axial extent is estimated from their weight and height in conjunction with statistical data regarding typical patient shapes. The subject's height and weight are measured and then compared to a patient collective or database which indexes maximum trans-axial extents according to statistics regarding height and weight. The ex-FoV is then determined to encompass this estimated patient size. Similarly, a typical maximum trans-axial extent can be estimated from a patient collective. This maximum extent is then used to determine the ex-FoV.

In another embodiment for determining the extent of the ex-FoV, the subject's extents can be estimated from other available image data, such as from previously acquired CT, MRI, SPECT, PET, or the like image representations. Similarly, the subject's extent can be estimated from concurrently or subsequently acquired projection data or reconstructed image data in which the imaged patient region does not move out of the examination region 18. For example, when performing a SPECT/CT or PET/CT acquisition with the imaging system 10, the SPECT/PET data or reconstructed image representation therefrom can be used to estimate the subject's outline and thus the subject's extents. Alternatively, additional CT projection data can be acquired for determining the subject's extents.

In another embodiment for determining the ex-FoV, a first reconstruction (possibly at low resolution) is performed in a very large FoV that is known to encompass the entire subject. For example, the FoV can be chosen at least as large as the scanner bore. The true patient outline can then be detected in this first reconstruction, and the extended FoV for the extended reconstruction can be chosen accordingly.

Once the ex-FoV is determined, the FoV is extended to encompass the ex-FoV in a number of ways depending on the intended use of the reconstruction and computational hardware limitations. In one embodiment, the voxel grid of the FoV is extended to at least one extended region outside the FoV up to the size of the ex-FoV. In other words, the number of voxels in the voxel grid of the FoV is increased while the size of each voxel remains the same. In another embodiment, if the extension of the FoV voxel grid is unachievable due to limitations on processing memory or processing time, the size or dimensions of each voxel of the FoV is increased while the number of voxels in the grid remains constant thus enlarging the spatial extent of the voxel grid.

After the location and the voxel grid of the ex-FoV are determined, an image representation of at least the FoV is generated, e.g., using an iterative reconstruction method, based on the ex-FoV and stored into CT image memory 36 for display on a graphical user interface 50. The graphic user interface 50 also includes a user input device by which a clinician or user interacts with a scan controller 52 to select scanning sequences and protocols, and the like.

In one embodiment, the ex-FoV is displayed with the user-selected FoV labeled. Additionally, a label can indicate the fully sampled FoV and possibly under-sampled regions. Alternatively, in the embodiment where the voxel grid of the FoV is extended, the reconstructed image representation can cropped to display just user defined FoV. In the embodiment where the voxel grid of the FoV is enlarged or extended and enlarged, or where the size of some or all of the voxels were enlarged, the reconstructed image representation is re-sampled back to the voxel size of the user selected FoV.

In another embodiment, the reconstructed ex-FOV is used to generate an attenuation map for correcting projection data acquired with the nuclear imaging scanner, such as SPECT or PET emission data. For accurate attenuation correction, it is important that the attenuation map represents the whole object to account for all attenuation during the acquisition. While this may not be the case for a user-defined FoV, complete coverage can be assured by using the described method and generating an attenuation map from the ex-FoV reconstruction. For example, the SPECT reconstruction processor 44 receives the reconstructed image representation of the ex-FOV and generates an attenuation map therefrom. The attenuation map is used to correct photon absorption and scatter by the anatomy of the subject.

Though the iterative reconstruction method utilizing an extended FoV to compensate for truncation errors is described for use in computed tomography image reconstruction, the method is also applicable in other imaging modalities for which iterative reconstruction methods are also performed. For example, the ex-FoV iterative reconstruction method can be applied to single slice CT, PET, SPECT, or the like. With regards to the imaging system 10, the SPECT reconstruction processor 44 can compensate for truncation errors in acquired SPECT emission data by utilizing the extended field of view along with an iterative reconstruction algorithm to generate SPECT image representations.

Figure 3:
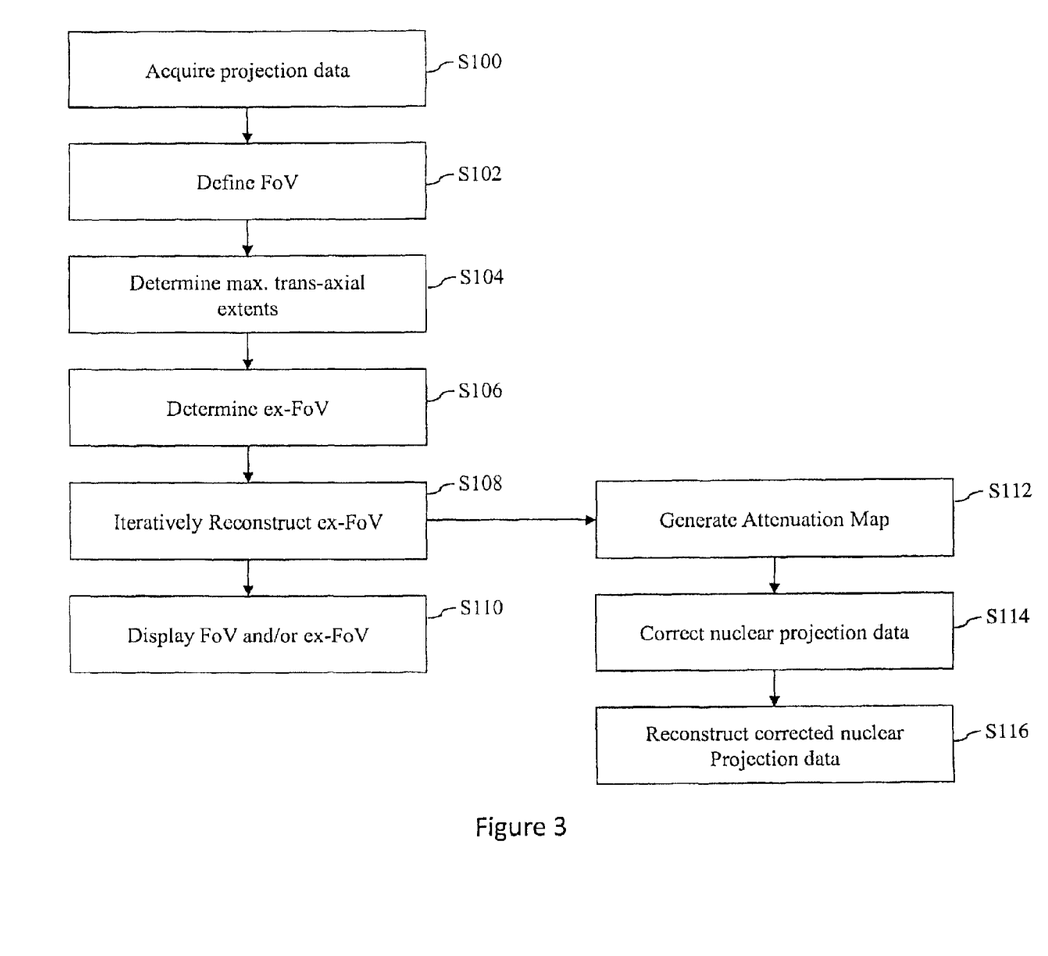
FIG. 3 is a flow chart of a method for truncation compensation for iterative reconstruction methods.

With reference to FIG. 3, a method for truncation compensation in an iterative reconstruction method is presented. The projection data of the subject is acquired S100 from the examination region 18. Using the graphical user interface 52, a clinician defines or selects a field of view S102. The subjects maximum trans-axial extents are determined S104 which are then used to determine an extended field of view S106 that encompass at least the determined maximum trans-axial extents and all attenuation or activity in the trans-axial direction. The extended field-of-view is iteratively reconstructed S108 using the acquired projection data.

The reconstructed image representation can be displayed S110 in multiple ways.

In the embodiment where the CT projection data is CT transmission data, the reconstructed CT image representation of the ex-FoV can be used to generated an attenuation map S112 which is used to correct nuclear projection data, e.g. SPECT/PET data S114, which is then reconstructed S116, e.g., iteratively, into an attenuation corrected nuclear image representation.

Figure 4A:
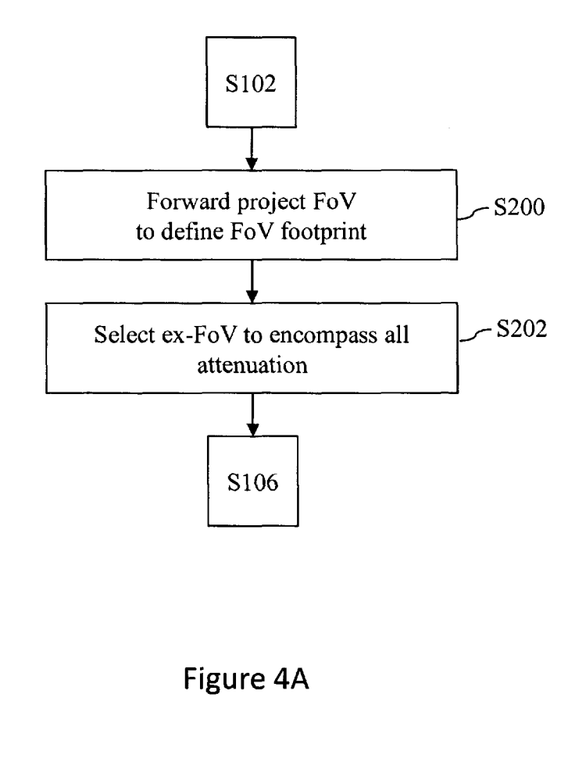
FIG. 4A-4D are flow charts of alternate methods for determining an extended field of view.

The subject's trans-axial extents can be determined a number of ways. In one embodiment illustrated in FIG. 4A the location of the ex-FoV, the FoV is forward-projected on the acquired X-ray projection data to define the FoV 'footprint' S200. The presence of a substantial amount of attenuation outside the FoV footprint in the trans-axial direction indicates truncation. The ex-FoV is then selected S202 large enough such that it encompasses all attenuation present in all projections in the trans-axial direction. This method may not be applicable if the subject extends beyond the detector in the trans-axial direction, i.e. the subject extends beyond the scanner FoV, in which case one of the following methods for determining the ex-FoV can be used.

Figure 4B:
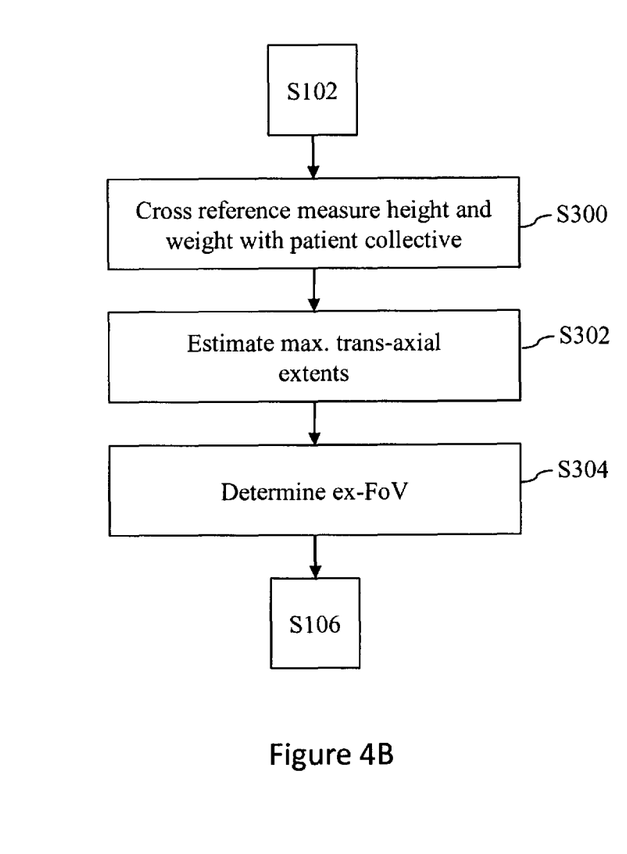
Figure 4C:
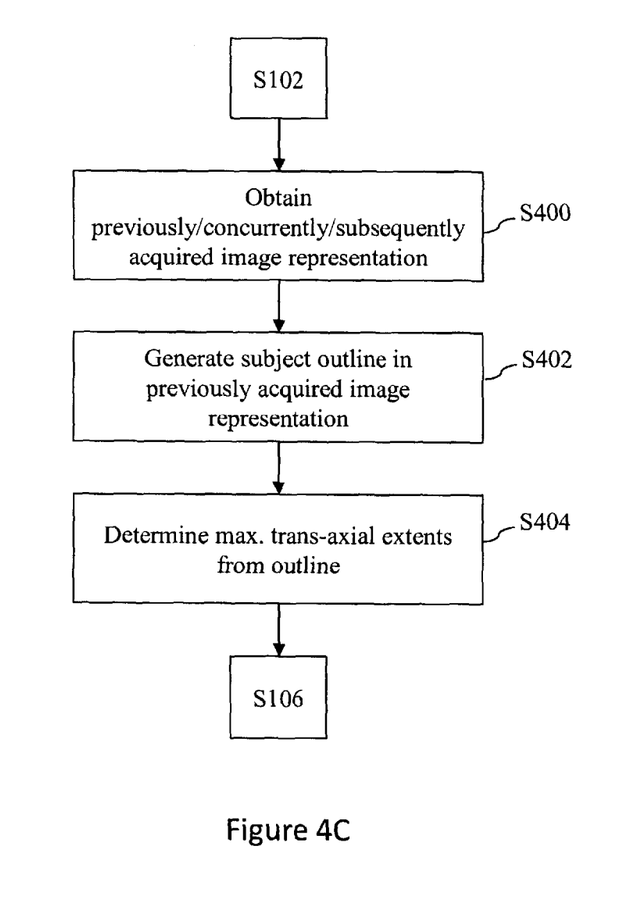

With reference to FIG. 4B, in another embodiment, the subject's trans-axial extents are estimated from his/her weight and height in conjunction with statistical data regarding typical patient shapes. The subject's height and weight are measured S300 and cross-referenced to a patient collective or database and the maximum trans-axial extents are estimated S302 according to statistics regarding height and weight. The ex-FoV is then determined S304 to encompass this estimated patient size. Similarly, a typical maximum trans-axial extent can be estimated from a patient collective. This maximum extent is then used to determine the ex-FoV.

Figure 5:
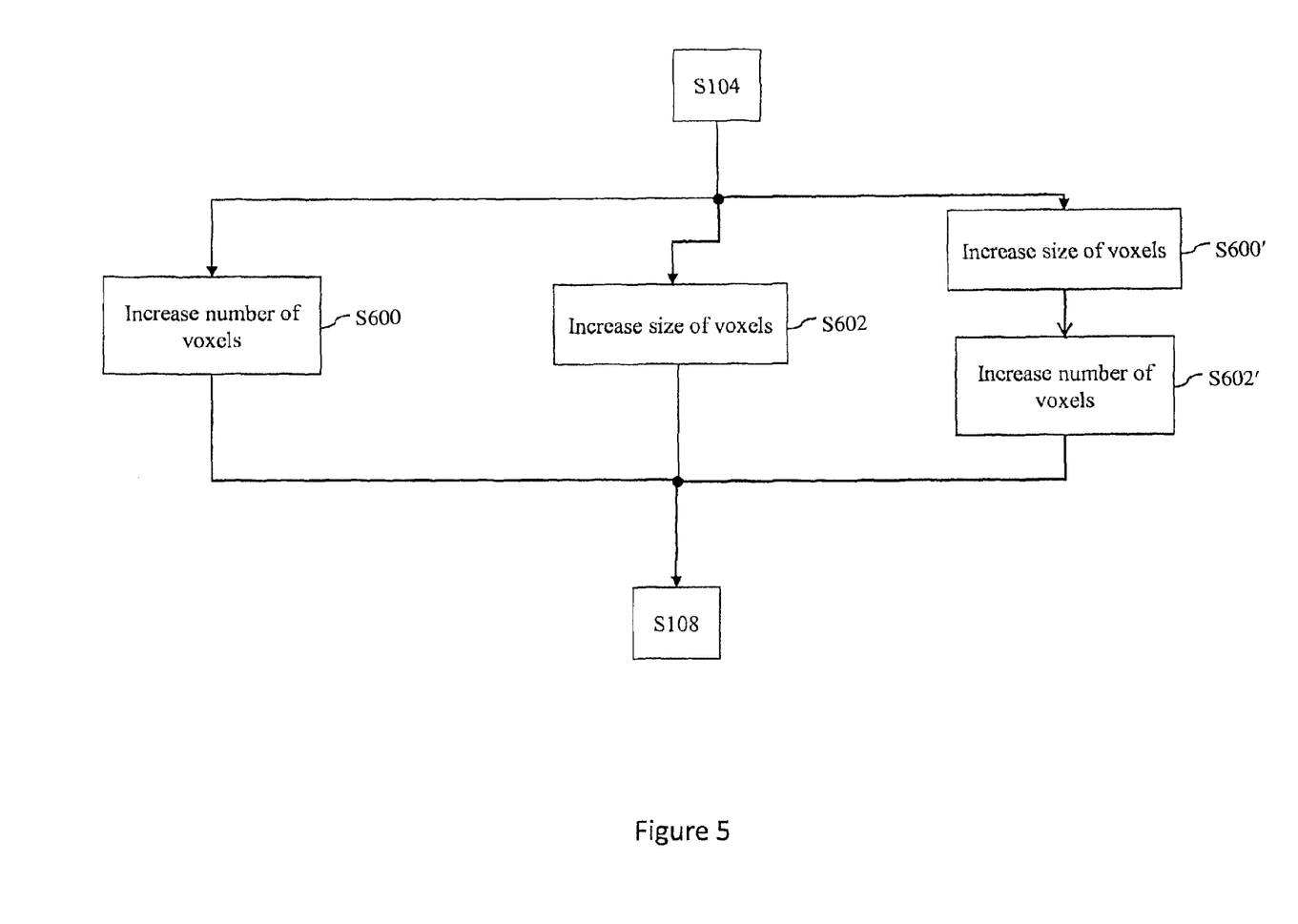
FIG. 5 is a flow chart of method for extending a voxel grid of a field of view into an extended field of view.

With reference to FIG. 5, the FoV can be extended to encompass the ex-FoV a number of ways depending on the intended use of the reconstruction and computational hardware limitations. In one embodiment, the voxel grid of the FoV is extended to at least one extended region outside the FoV up to the size of the ex-FoV. In other words, the number of voxels in the voxel grid of the FoV is increased S600 while the size of each voxel remains the same. In another embodiment, if the extension of the FoV voxel grid may be unachievable due to limitations on processing memory or processing time, the size or dimensions of each voxel of the FoV is increased S602 while the number of voxels in the grid remains constant thus enlarging the spatial extent of the voxel grid. In another embodiment, a combination of an increase in size S600' and an increase in the number S602' is used.

Figure 4D:
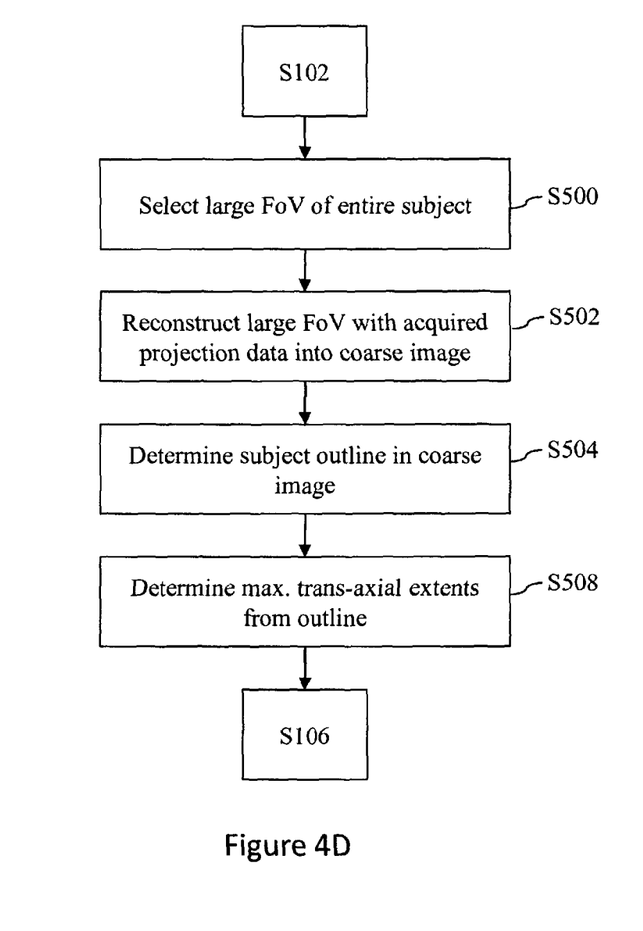

With reference to FIG. 4D, a first reconstruction S502, using a low resolution and/or a faster algorithm such as FBP, is performed in a selected very large FoV S500 that is known to encompass the entire subject. For example, the FoV is chosen at least as large as the scanner bore. The true patient outline is determined S504 in this first reconstruction, and the extended FoV for the extended reconstruction is chosen according to the maximum trans-axial extents of the determined outline.

With reference to FIG. 5, the FoV can be extended to encompass the ex-FoV a number of ways depending on the intended use of the reconstruction and computational hardware limitations. In one embodiment, the voxel grid of the FoV is extended to at least one extended region outside the FoV up to the size of the ex-FoV. In other words, the number of voxels in the voxel grid of the FoV is increased while the size of each voxel remains the same. In another embodiment, if the extension of the FoV voxel grid may be unachievable due to limitations on processing memory or processing time, the size or dimensions of each voxel of the FoV is increased while the number of voxels in the grid remains constant thus enlarging the spatial extent of the voxel grid.

The various computational and control components disclosed herein can be implemented in various ways, for example by a computer or other device including a digital processor and programmed or including firmware to perform the disclosed processing, or by hybrid or analog circuitry configured to perform the disclosed processing or portions thereof, or so forth. In some embodiment, the computational components may be embodied by a computer having suitable firmware or programming. The techniques disclosed herein can be implemented by a processor other hardware, and/or can be embodied as a storage medium storing instructions that, when executed by such a processor or other hardware, perform the disclosed methods. Such a storage medium may be embodied by one or more types of storage media, such as one or more of: a magnetic disk, an optical disk; a FLASH memory or other electrostatic memory; a random access memory (RAM); a read-only memory (ROM); DVD; or so forth.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

Having thus described the preferred embodiments, the invention is now claimed to be:

1. An imaging method comprising:
   receiving radiation transmission image data of a subject situated in an examination region acquired with a tomographic imaging modality;
   defining a field-of-view (FoV) with a voxel grid in a trans-axial direction;
   determining the subject's maximum trans-axial extents;

generating an extended FoV by extending the voxel grid of the FoV to at least one extended region outside the FoV that encompasses at least the determined maximum trans-axial extents and attenuation in the trans-axial direction;

reconstructing the acquired radiation transmission data into an attenuation map of the extended FoV;

receiving nuclear image data of the subject acquired with a radiation emission imaging modality;

wherein the radiation transmission image data from the first imaging modality is acquired concurrently or in close temporal proximity with the nuclear image data of the radiation emission imaging modality; and reconstructing the nuclear image data including using the attenuation map.

2. A method of tomographic imaging comprising:

acquiring projection tomographic image data of a subject situated in an examination region with a first imaging modality;

defining a field-of-view (FoV) with a voxel grid in a trans-axial direction;

determining the subject's maximum trans-axial extents;

generating an extended FoV by extending the voxel grid of the FoV to at least one extended region outside the FoV that encompasses at least the determined maximum trans-axial extents and attenuation in the trans-axial direction wherein generating the extended FoV includes:

forward projecting the FoV onto the acquired projection data to define a FoV footprint; and extending the FoV footprint such that it includes all attenuation or activity present in the projection data; and reconstructing the acquired projection tomographic image data into a tomographic image representation of the extended FoV.

3. A method of imaging comprising:

acquiring radiation projection tomographic image data of a subject situated in an examination region with a tomographic imaging modality;

defining a field-of-view (FoV) with a voxel grid in a trans-axial direction;

determining the subject's maximum trans-axial extents;

generating an extended FoV by extending the voxel grid of the FoV to at least one extended region outside the FoV that encompasses at least the determined maximum trans-axial extents and attenuation in the trans-axial direction, wherein the step of extending the FoV includes at least one of:

increasing the number of voxels in the FoV to encompass the at least one extended region, or increasing the size of each voxel in the FoV to encompass the at least one extended region; and reconstructing the acquired projection tomographic image data into a tomographic image representation of the extended FoV, wherein the reconstructed tomographic image representation includes the FoV and the extended regions, the method further including:

resampling the reconstructed tomographic image representation to decrease the voxel size to that of the FoV voxel grid; and displaying the resampled tomographic image representation such that the defined FoV is visible.

4. The method according to claim 3, wherein the reconstructing step includes iteratively reconstructing the acquired projection data into the tomographic image representation.

5. The method according to claim 3, further including:

generating an attenuation map based on the reconstructed tomographic image representation of the extended FoV;

generating an emission data set of the subject acquired with a nuclear imaging modality; and reconstructing the emission image data including using the attenuation map.

6. The method according to claim 3, wherein the subject's extents are estimated according to at least one of:

at least one of the subject's weight, the subject's height, and a patient collective database;

a previously acquired image of the subject;

by defining a coarse voxel grid in a FoV which is known to be greater than the subject's trans-axial extents, reconstructing the large FoV into a coarse image representation, the coarse image representation having a resolution lower than the reconstructed image representation, and determining the subject's trans-axial extents based on the coarse image representation; and by forward projecting the FoV onto the acquired projection tomographic image data to define a FoV footprint, and extending the FoV footprint such that it includes all attenuation or activity present in the projection data.

7. The method according to claim 3, wherein the voxels of the FoV and the voxels of the at least one extended region have a different size.

8. A non-transitory computer-readable medium carrying software to control one or more processors to perform the method according to claim 3.

9. A processor programmed to perform the method according to claim 3.

10. An imaging scanner comprising:

a radiation transmission tomographic imaging scanner which acquires projection tomographic image data of a subject situated in an examination region using a tomographic radiation imaging modality;

at least one processor programmed to perform the method of claim 3.

11. The imaging scanner according to claim 10, wherein the radiation transmission tomographic imaging scanner includes a cone-beam computed tomography scanner which includes an offset detector.

12. The imaging scanner according to claim 11, further including:

a nuclear imaging scanner which acquires nuclear data of the subject situated in the examination region; and wherein the processor is further programmed to:

generate an attenuation map based on the tomographic image representation of the extended FoV; and reconstruct the nuclear data using the attenuation map.

13. The imaging scanner according to claim 10, wherein the processor is programmed to determine the subject's maximum trans-axial extents from at least one of:

from the subject's weight, the subject's height, or a patient collective database from a previously acquired image; or by defining a coarse FoV which is known to be greater than the subject's trans-axial extents, reconstructing the coarse FoV into a coarse image representation, the coarse image representation having a resolution lower than the tomographic image representation, and determining the subject's trans-axial extents based on the coarse image representation; or forward projecting the FoV onto the acquired radiation projection tomographic image data to define a footprint and extending the footprint to include all attenuation or activity present in the acquired radiation projection tomographic image data.

14. An apparatus comprising:
means for defining a field-of-view (FoV) with a voxel grid in a trans-axial direction;
means for determining the subject's maximum trans-axial extents;
means for generating an extended FoV by extending the voxel grid of the FoV to at least one extended region outside the FoV that encompass at least the determined maximum trans-axial extents and all attenuation in the trans-axial direction, wherein the means for extending the FoV includes at least one of:
means for increasing a number of voxels in the FoV to encompass the at least one extended region, or
means for increasing a size of each voxel in the FoV to encompass the at least one extended region;
means for iteratively reconstructing the acquired projection data into an image representation of the extended FoV, wherein the reconstructed image presentation includes the FoV and the extended regions;
means for resampling the reconstructed image representation to decrease the voxel size or the number of voxels to that of the FoV voxel grid; and
means for displaying the resampled image representation such that the defined FoV is visible.

15. An imaging system comprising:
one or more processors configured to:
receive a first imaging modality data set of a subject situated in an examination region,
receive a field-of-view (FoV) in a trans-axial direction of the subject to be imaged using a second imaging modality, the FoV being defined by an initial voxel grid,
determine maximum trans-axial extend of the subject, wherein the maximum trans-axial extent exceeds the FoV,
extend the voxel grid to encompass at least the determined maximum trans-axial extent by at least one of increasing a number of voxels in the initial voxel grid or increasing a size of the voxels in the initial voxel grid such that the extended voxel grid encompasses at least the maximum trans-axial extent,
reconstruct the first imaging modality data set into a first modality image of the extended grid,
resample voxels of the extended voxel grid to form a resampled voxel grid of a size of the FoV with the same number and size of voxels as in the initial voxel grid,
receive a second imaging modality data set corresponding to the FoV of the subject,
reconstruct the second modality imaging data set into a second modality image of the FoV of the subject using the resampled voxel grid; and
a display device configured to display the second modality image.

16. The imaging system according to claim 15, wherein the second imaging modality data set includes a nuclear imaging data set and wherein the reconstruction of the nuclear imaging data set by the one or more processors includes:
attenuation correcting the nuclear imaging data set using the reampled voxel grid.

17. The imaging system according to claim 16, further including:
a nuclear scanner configured to generate the nuclear imaging data set.

18. The imaging system according to claim 15, further including:
an imaging system configured to concurrently generate the first and second imaging modality data sets.

* * * * *